US007250195B1

(12) United States Patent
Storey et al.

(10) Patent No.: US 7,250,195 B1
(45) Date of Patent: Jul. 31, 2007

(54) MOLECULAR PLASMA DEPOSITION OF COLLOIDAL MATERIALS

(75) Inventors: Daniel M. Storey, Longmont, CO (US); Terrence S. McGrath, Longmont, CO (US); Tushar M. Shimpi, Longmont, CO (US)

(73) Assignee: Ionic Fusion Corporation, Plymouth, MN (US)

( * ) Notice: Subject to any disclaimer, the term of this patent is extended or adjusted under 35 U.S.C. 154(b) by 0 days.

(21) Appl. No.: 11/623,411

(22) Filed: Jan. 16, 2007

Related U.S. Application Data (60) Provisional application No. 60/777,104, filed on Feb. 27, 2006.

(51) Int. Cl.
*B05D 1/04* (2006.01)

(52) U.S. Cl. .................... 427/475; 427/2.24; 427/2.28; 427/458; 427/569

(58) Field of Classification Search ................ 427/475, 427/2.24, 2.28, 458, 569
See application file for complete search history.

(56) References Cited

U.S. PATENT DOCUMENTS

| | | | | |
|---|---|---|---|---|
| 3,274,089 | A | 9/1966 | Wolinski | |
| 3,415,683 | A | 12/1968 | Coffman et al. | |
| 4,145,386 | A | 3/1979 | Rosenthal | |
| 4,520,754 | A | 6/1985 | Gange et al. | |
| 4,615,906 | A | 10/1986 | Kolbe et al. | |
| 5,336,518 | A | 8/1994 | Narayanan et al. | |
| 5,427,669 | A | 6/1995 | Drummond | |
| 5,733,360 | A | 3/1998 | Feldman et al. | |
| 5,876,753 | A | 3/1999 | Timmons et al. | |
| 5,928,916 | A | 7/1999 | Keogh et al. | |
| 6,143,354 | A | 11/2000 | Koulik et al. | |
| 6,239,553 | B1 | 5/2001 | Barnes et al. | |
| 6,632,470 | B2 | 10/2003 | Morra et al. | |
| 2006/0177573 | A1 * | 8/2006 | Pui et al. | 427/180 |
| 2006/0208741 | A1 | 9/2006 | Hiraoka | |

FOREIGN PATENT DOCUMENTS

| | | |
|---|---|---|
| WO | WO 2002-28548 | 4/2002 |
| WO | WO 2003-084682 | 10/2003 |
| WO | WO 2006-046003 | 5/2006 |

OTHER PUBLICATIONS

Poncin-Epaillard, F., et al., Surface engineering of biomaterials with plasma techniques, J. Biomater. Sci. Polymer Edn, 2003, vol. 14(10), pp. 1005-1028.
Inculet, I.I., et al., Q/M distribution in pulsed corona powder coating spray cone, 1995, IEEE, 1289-1294.
Pan, P., et al., Nanoelectrospray Ionization of protein mixtures: solution pH and protein pl, Analytical Chem., 2004, vol. 76, 1165-1174.
Storey, D.M., Breakup of Biomolecules through low-energy ion Bombardment, Masters Theis, University of Missouri-Rolla, 1998.

* cited by examiner

*Primary Examiner*—Fred J. Parker
(74) *Attorney, Agent, or Firm*—Saliwanchik, Lloyd & Saliwanchik (57) ABSTRACT

A molecular plasma discharge deposition method for depositing colloidal suspensions of biomaterials such as amino acids or other carbon based substances onto metal or non-metal surfaces without loss of biological activity and/or structure is described. The method is based on generating a charged corona plasma which is then introduced into a vacuum chamber to deposit the biomaterial onto a biased substrate. The deposited biomaterials can be selected for a variety of medical uses, including coated implants for in situ release of pharmaceuticals.

20 Claims, 2 Drawing Sheets

MOLECULAR PLASMA DEPOSITION OF COLLOIDAL MATERIALS

This application claims benefit of U.S. provisional application Ser. No. 60/777,104 filed Feb. 27, 2006, the entire contents of which are herein incorporated by reference.

BACKGROUND OF THE INVENTION

1. Field of the Invention

The invention relates to an apparatus and process for using corona discharge to deposit colloidally suspended molecules onto substrate surfaces. The method is applicable to deposition of organic and inorganic compounds, particularly to proteins and related biological compounds of interest onto selected substrates with little or no loss of native structure or activity.

2. Description of Background Art

There is increasing interest in the immobilization of biologically active substances onto various substrates without significant alteration of function or desired activity. Surfaces coated with antibiotics, for example, are typically prepared by dipping or paint processes, which often result in poor adhesion, incomplete surface wetting or poor adhesion.

Ionic plasma deposition (IPD) methods have been extensively developed and used in coating processes, predominately with the objective of producing highly adhesive coatings and customized surface characteristics. Attention has recently focused on preparing coated surfaces that are biocompatible, such as those suitable for medical implants where the coatings enhance cell adhesion or where antimicrobial coatings are important in avoiding potential sepsis after surgery.

Corona discharge is a well-known phenomenon which has long been observed in nature and traditionally used in a number of commercial and industrial processes. It is currently used in ozone production, control of surface generated electrical charges and in photocopying. Electric corona discharge has also been used to modify surfaces, particularly for plastic articles to improve surface characteristics, as described in U.S. Pat. No. 3,274,089. An electrostatic coating process involving a corona discharge of a liquid or powdered material is described as a coating method, U.S. Pat. No. 4,520,754.

A corona is generated when the potential gradient is large enough at a point in the fluid to cause ionization of the fluid so that it becomes conductive. If a charged object has a sharp point, the air around that point will be at a much higher gradient than elsewhere. Air near an electrode can become ionized (partially conductive), while regions more distant do not. When the air near the point becomes conductive, it has the effect of increasing the apparent size of the conductor. Since the new conductive region is less sharp, the ionization may not extend past the local region. Outside the region of ionization and conductivity, the charged particles slowly find their way to an oppositely charged object and are neutralized.

Corona discharge usually involves two asymmetric electrodes; one highly curved, e.g., a needle tip or a small diameter wire, and one of low curvature, e.g., a plate, or a ground. The high curvature ensures a high potential around the electrode, providing for the generation of a plasma. If the geometry and gradient are such that the ionized region continues to grow instead of stopping at a certain radius, a completely conductive path may be formed, resulting in a momentary spark or a continuous arc.

Coronas may be positive or negative. This is determined by the polarity of the voltage on the highly-curved electrode. If the curved electrode is positive with respect to the flat electrode a positive corona exists; otherwise the corona is negative. The physics of positive and negative coronas are strikingly different. This asymmetry is a result of the great difference in mass between electrons and positively charged ions, with only the electron having the ability to undergo a significant degree of ionizing inelastic collision at ordinary temperatures and pressures.

Corona discharge systems have been used to activate chemical compounds, generally to deposit polymers and polymerizable monomers formed within a corona discharge onto surfaces as protective coatings; as described in U.S. Pat. No. 3,415,683. A corona discharge reactor for chemically activating constituents of a gas stream; e.g, sulfur and nitrogen oxides and mercury vapor, is described in U.S. Pat. No. 5,733,360. The reactor is designed to pulse generate a corona by applying high voltages pulses for up to 100 nanoseconds to a plurality of corona discharge electrodes.

WO 2006/046003 describes several methods for coating substrates involving use of a plasma, including use of low pressure pulsed plasma to introduce monomers or monomers in combination with free radical initiators to initiate polymerization on a suitable substrate. An atmospheric pressure diffuse dielectric barrier discharge assembly is used into which an atomized liquid containing the monomers is introduced so that a coating material is formed from atomized drops of from 10 to 100 μm. An atmospheric pressure glow discharge plasma generating apparatus using radiofrequency energized electrodes is described in WO 03/084682.

A plasma coating apparatus and method are described in WO 02/28548. Liquid or solid atomized coating forming materials are introduced into a plasma discharge at atmospheric pressure and are useful for organic coatings such as polyacrylic acid or perfluoro compounds in addition to silicon-containing monomers.

Corona effects are not always considered beneficial and may in fact cause arcing, or the breakdown of the corona. In addition to this breakdown, the corona effect may be too strong to successfully only singly charge a complex molecule. When molecules ionize at a higher level, they may break apart and lose structural and functional properties.

One disadvantage of depositing materials generated in plasmas from liquid solutions is that any solvent present is typically deposited along with the intended material, creating unintended structures. For most processes where corona discharge can occur during plasma generation, efforts are usually taken to reduce the corona effect rather then using this effect as a deposition technique.

Deficiencies in the Art

The loss of functional and/or physical properties of plasma surface deposited organic molecules points to the need to develop methods of maintaining desirable biological activities of immobilized materials. Attempts to engineer biological coatings on a range of substrates, such as plastics, metals, polymers, and ceramics have met with limited success and generally have failed to deposit biologically active agents on surfaces without compromising desired activity.

SUMMARY OF THE INVENTION

The present invention relates to a molecular plasma deposition method for non-destructively coating biological agents on substrate surfaces. The method employs a modified IPD apparatus utilizing electric fields and vacuum to lay down a biological coating on virtually any conductive surface, and many non-conductive surfaces. A corona plasma molecular discharge is generated from a highly charged conductive tip. The method is applicable to deposition of a wide range of organic and inorganic materials, which are dispersed as solutions or suspensions from the conductive tip.

There are several features of the described method that differ from conventional uses of either corona discharges or ionic plasma depositions. The method employs solutions or suspensions of the materials to be deposited. This allows a wide range of organic as well as inorganic materials to be used, including elements and compounds. The liquids are atomized through a small pointed orifice maintained at a high voltage so that an ionized plasma is dispensed from the orifice. In a subsequent step of the method, the ionized plasma is directed into an evacuated chamber where an oppositely biased substrate is located, causing the material to be deposited where it becomes bonded to the surface of the substrate.

An important feature of the method is the deposition of biologically active agents onto a surface with little or no alteration of structure or functional characteristics. The method is equally applicable to inorganic materials, elements and select compositions, which are not otherwise amenable to coating processes. Due in part to the wide range of materials that can be deposited by this method, the ability to modify or bio-engineer different surfaces is significantly expanded.

The known characteristics of the corona effect under atmospheric conditions and the advantages of ionic plasma deposition (IPD) methods in coating processes have been used to develop a novel corona plasma deposition process and coating method. An important aspect of the invention is the ability to use a corona generated from a liquid or colloidal composition to deposit a coating consisting of only the desired component, without the solvent in which the material to be deposited is dissolved or dispersed. Moreover, maintaining the original structural properties of a wide range of materials deposited from a corona generated molecular plasma was not expected, most notably as shown with a polypeptide enzyme, which maintained catalytic activity after the molecular plasma deposition. Atomic bonds are not broken during the deposition process, a factor in retaining activity and/or structural integrity of the deposited product.

In one embodiment, the process is carried out in part under atmospheric or partial pressure, and in part under vacuum. The deposition apparatus is designed to generate a corona from a solution or suspension introduced through a narrow electrified opening, such that a plasma is produced in front of a small aperture that opens into a vacuum chamber housing a substrate. Depending on the charge produced on the material dispersed in the corona plasma, the substrate is wired as an oppositely charged electrode on which the plasma particulates will deposit.

The basic structural characteristics of the deposited materials tested are not affected by the thickness of the deposit. This is in contrast to the results obtained by Storey (Breakup of Biomolecules through low-energy ion Bombardment, Master's thesis, University of Missouri, Rolla, 1998) where more than 40 or so monolayers of glycine or arginine deposited by flooding a solution of the amino acids on gold caused loss of structure, as indicated by increasing difficulty in detecting the carboxyl groups of the deposited amino acids as sample thickness increased. The disclosed molecular plasma method allows thickness to be controlled from a mono-layer of desired material to micron thickness; i.e., 2-200 microns thick while maintaining structure and activity.

The apparatus for molecular plasma deposition can be modified to accommodate a partial vacuum around the conductive tip where the corona is generated. This permits more efficient volatilization of the solvent suspending the dissolved or suspended material, so that only the material itself is drawn into the vacuum chamber housing to be deposited on the substrate and little if any solvent is present in the coating. This is necessary because, in biological applications, if the suspending solvent is also co-deposited, it may cause an adverse interaction with the deposited material. For example, if a protein that one desires to deposit on a medical implant device is dissolved in methyl alcohol, and deposited without volatilization of the alcohol before being placed in the body, the residual alcohol may cause serious physiological problems. Where little or no solvent is drawn into the chamber, it is convenient to generate the corona under atmospheric pressure conditions.

As discussed, the new method is a molecular plasma procedure for deposition of a biomolecule onto a substrate. A corona discharge plasma is generated under atmospheric or partial vacuum conditions from a liquid solution or suspension. The suspension is preferable colloidal suspension for materials that have low solubility in organic or aqueous solvents. Deposited materials may be an element, a compound, or any of a number of biomolecules. The liquid solution or suspension is ejected from a conductive point source at a high potential gradient and the resulting corona discharge is directed through an opening into an evacuated chamber where the ionized molecular plasma will be deposited onto a substrate which is maintained at an induced potential opposite from the relatively high potential at the point source where the corona is generated.

Generally, the conductive tip or point from which the colloidal suspension is ejected provides a means for atomizing the solution or liquid suspension, so that there is ready formation of a corona discharge at the high voltage tip. In many applications, one will prefer to introduce the solution or liquid suspension from the tip under atmospheric conditions, but a low or partial vacuum can also be used, preferably 100 mTorr or higher. The charged plasma then passes through a hole or orifice into an evacuated chamber; e.g., at 40 mT or less, housing a substrate held at a voltage substantially opposite to the voltage at the conductive tip. The ionized molecules in the corona plasma then deposit onto the substrate in the chamber, which is at a lower pressure than at the conductive tip where the corona is generated.

It is important to recognize that the substrate is under vacuum, typically less than 100 mTorr, preferably 40 mTorr or lower, and that if the plasma corona is formed at a tip also under reduced pressure, the substrate must be in a reduced pressure atmosphere such that the plasma can be effectively drawn into the substrate housing and deposited onto the substrate. The vacuum around the substrate is typically in the range of 40-0.1 mTorr. Additionally, the substrate must be oppositely biased in order to effect deposition from the ionized molecular plasma, which may be positive or negative depending on the material in the colloidal suspension. The ions formed in the discharge may be positive or negative. This discharge will determine the bias of the substrate; e.g., if a positive corona is used, the substrate must be negatively biased.

The amount of bias imposed on the substrate will depend on the substrate and on the area for deposition. In the examples provided herein, the substrates are approximately 4 cm². The bias of the substrate is constant regardless of the size of the deposition; however, the larger the area, the higher is the current necessary to maintain constant voltage. Voltage applied to the substrate may range as high as 60 kV, which may be positively or negatively biased; i.e., opposite to the voltage at the conductive tip where the corona is generated. Typical voltages range from +15 kV through −15 kV. Where the substrate is grounded, the voltage will be zero at the substrate.

The method relies in part on efficiently generating an ionized plasma. This is accomplished by atomizing a liquid solution or suspension of the material desired for deposition through a sharp orifice or tip. This is typically a small diameter tube or needle that is imposed with a high voltage. An exemplary high voltage on an 18 gauge metal needle with an inside diameter of approximately 0.83 mm, for example, may be about −5000 volts. In this example, the voltage applied to the substrate is typically in the range of about 5000 or less volts or is zero if connected to ground.

Yet another aspect of the invention is the ability to control the corona effect for more efficient processing; e.g., for engineering surfaces. The method takes advantage of the physics of the corona effect to deposit ionized material onto a substrate, so that the material is ionically or covalently bonded to a substrate surface. This is a fast, easy way to produce an adherent coating and to structure a surface using a non-destructive technique.

The described apparatus can be used to effectively deposit a wide range of materials without significantly altering the physical, functional or chemical characteristics, by generating material into a corona plasma from a liquid solution or suspension. Materials such as proteins are preferably ionized from colloidal suspensions, due to their limited solubility in most solvents. Thymine, cytosine, adenine and guanine with respective water solubilities of 4.5 g/L, insoluble, 0.5 g/L and insoluble, are more efficiently deposited as aqueous suspensions. Almost any organic or inorganic material can be dissolved or suspended in some solvent or mixture of solvents. Materials include proteins, amino acids, peptides, polypeptides, nucleic acids and nucleic acid bases such as purines and pyrimidines, and the like. Examples of inorganic materials include compounds such as metals and metal oxides, e.g., copper oxide, elements, including carbon. In general, biological and non-biological materials that can be prepared as a solution or liquid suspension will be suitable materials for deposition. While colloidal suspensions may be preferable for some biomolecules, microparticulate suspensions may also be suitable, depending on the material, thus creating ionized molecular plasmas from liquids containing micron- or larger sized particles. Examples of material that are preferably deposited from molecular plasmas generated from colloidal suspensions include, but are not limited to: DNA, RNA, graphite, antibiotics, growth factors, growth inhibitors, viruses, inorganic compounds, catalysts, enzymes, organic compounds, and elements. Catalase is one example of a polypeptide enzyme that can be deposited by this method without loss of catalytic activity. Other proteins expected to be deposited by this method without loss of biological activity include SNAP-tag fusion proteins, hAGT fusion proteins glucose binding protein, glutamine binding protein and lactate dehydrogenase. Oxidodreductases and oxidases such as glucose oxidase are also expected to be deposited without loss of activity. Nucleotide bases such as guanine, thymine, adenine, cytosine, and uracil are examples of DNA and RNA bases that can be deposited onto a substrate from a corona generated plasma.

The solutions and liquid suspensions that are suitable for deposition may be formulated from any of a number of aqueous or organic solvents, including pure water, alcohol and water/alcohol mixtures. Some materials may be prepared in less common solvents, such as DMSO or glycols. For preferred practice of the deposition procedure, one will select a solvent or combination of solvents in which the material can be dissolved or suspended, preferably as a colloidal suspension, and which does not give rise to problems such as toxic or explosive fumes.

Definitions

Biomolecules are intended to include compounds and agents that have some biological effect or use in the body and may include, without limitation, proteins, peptides, amino acids, nucleic acids and compounds having drug activity or related to drug activity. As used herein, biomolecules also include carbon and carbon based compounds and elements and compounds such as copper oxide that may be used as coating materials on medical devices.

Colloidal particles are finely divided particles approximately 10 to 10,000 angstroms in size, dispersed within a continuous medium. The particles are not easily filtered and settle slowly over a period of time.

Nano particles are about 100 nanometers or less in size.

Ionic Plasma Deposition (IPD) is the vacuum deposition of ionized material generated in a plasma, generally by applying high voltage or high current to a cathode target where the ionized plasma particles are deposited on a substrate which acts as an anode.

A corona is produced by a process by which a current, perhaps sustained, develops from an electrode with a high potential in a neutral fluid, such as air, by ionizing the fluid to create a plasma around the electrode. The ions generated eventually transfer a charge to nearby areas of lower potential, or recombine to form neutral gas molecules.

Voltage bias is the potential, relative to earth ground, at which substrate is held. Potential ranges from zero to 15,000 volts and can be positive or negative. The potential on the substrate for biasing depends on the potential of the corona and is typically equal and opposite of this potential. Voltage may be as high as 60 kV but more typically is in the range of 5-10 kV. Where the corona plasma is +5000 volts, bias voltage for the substrate will be −5000 volts, all relative to earth ground.

As used herein, substantial or substantially means that a range is intended, on the order of plus or minus ten percent and is not intended to be limited to an exact number; for example, substantial function may include different or less than original function.

BRIEF DESCRIPTION OF THE DRAWINGS

FIG. 1 is a sketch of the molecular plasma deposition apparatus: vacuum chamber 1; high voltage power supply 2, substrate holder 3; substrate 4; high voltage power supply 5; needle 6; feeder tube to needle 7; orifice 15 into reservoir 8; colloidal liquid suspension 9.

FIG. 2 is a sketch of a modification of the apparatus of FIG. 1: vacuum chamber 1; high voltage power supply 2; substrate holder 3; substrate 4; high voltage power supply 5; needle 6; feeder tube 7; orifice 15 into reservoir 8; liquid suspension 9; secondary chamber 10; secondary chamber gas supply 11; secondary chamber gas supply line 12; pressure regulator 13; gas line from regulator 14.

FIG. 3 is a representation of the electric field equation for a point charge.

DETAILED DESCRIPTION

Figure 1:
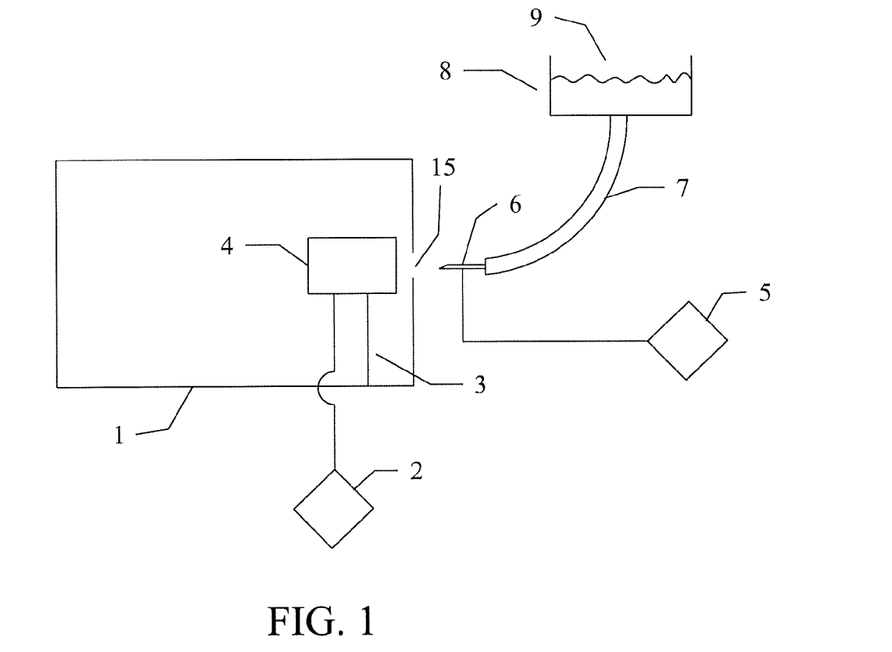
Figure 2:
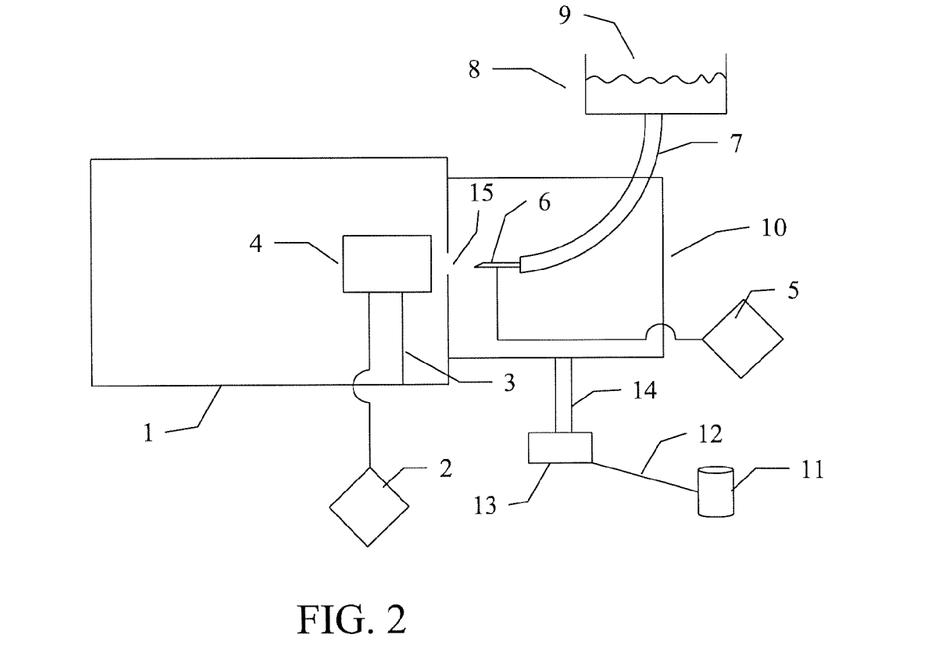

The present invention takes advantage of the corona effect and the effect of corona discharge in creating a charged plasma that can be directed to a substrate surface. The basic apparatus is shown in FIG. 1 and FIG. 2. In an exemplary procedure, a high voltage of 5 kV or higher is applied to the needle or other hollow bore, sharp pointed, conductive material. A solution or liquid suspension is passed through the hollow bore. The high electric field at the tip of the needle causes atomization of the liquid as the result of the corona effect. The molecules in the solution or suspension become charged, yet remain intact. The needle is positioned in front of a grounded, differentially pumped high vacuum system with a small hole in the chamber housing the substrate. The substrate is placed inside the evacuated chamber at a potential opposite or nearly opposite to that imposed on the needle or is set to ground (zero). The charged molecules within the corona travel through the opening toward the substrate and become deposited or attached to the substrate, becoming ionically or covalently bonded.

The entire apparatus is enclosed in an environmentally controlled chamber into which selected gases such as oxygen or nitrogen may be introduced; for example, if oxidation is desired, to control deposition rate, or to perform the deposition in an inert atmosphere. Mixtures of gases may be introduced, including other inert gases such as xenon, argon, helium or combinations of gases.

The molecular plasma generation process can also be run at lower than atmospheric pressures, i.e., under reduced pressure, in the presence of gases other than atmospheric, (e.g., argon or oxygen background atmosphere). When the molecular plasma at the conductive tip is generated under reduced pressure, the pressure in the chamber housing the substrate must be lower so that the plasma discharge passes readily through the opening into the chamber housing the substrate, as shown in FIG. 1.

As shown in FIG. 1, the molecular plasma generation apparatus provides a system for producing a plasma discharge under atmospheric conditions by passing a liquid colloidal suspension 9 through a discharge needle 6 at a high voltage 5. The resulting atomized liquid forms an ionized plasma in the atmosphere. The plasma passes through an orifice 15 in the vacuum chamber 1 housing the substrate 4 on the substrate holder 3. A power supply 2 provides voltage to the substrate 4 at a voltage opposite to that provided by the power supply 5 to the discharge needle 6.

FIG. 2 illustrates an alternative embodiment of a system for producing an ionized plasma discharge. A reservoir 8, feeds a solution or liquid suspension of the material 9 through an orifice 15 for deposition of the colloidal material on the substrate 4. The liquid is passed through the highly charged needle 6 from the power supply 5. In this embodiment, the feeder and needle are housed in a second chamber 10 which can be pressure regulated by a pressure control 13 through the opening 14 into the secondary chamber. The atmosphere within the secondary chamber 10 can be modified from a gas container 11 having a conduit 12 passing through the regulator 13. The vacuum chamber 1 is maintained at a lower pressure than in chamber 10. The substrate 4 is biased using the power supply 2 at a voltage opposite to that supplied by power supply 5 to the needle 6.

Liquid suspensions or solutions may be prepared in organic or inorganic liquids, which should not be toxic or flammable. Most materials are preferably prepared as aqueous solutions or may be prepared in organic acids such as acetic acid, propionic acid, halogen substituted acetic acid, oxalic acid, malonic acid and/or hydroxycarboxylic acids alone or with water. Liquid mixtures may include salts or organic/water miscible preparations. Examples of alcohols include ethanol, methanol, and ketones such as acetone, DMF, THF and methylethylketone. Amino acids, for example, may be water soluble at low concentrations but form colloidal suspensions at higher concentrations. Lysine and threonine are highly water soluble while tyrosine has a limited solubility of about 0.045 g/100 ml at 25° C.

BACKGROUND DESCRIPTION OF CORONAS AND ELECTRICAL DISCHARGES

Figure 3:
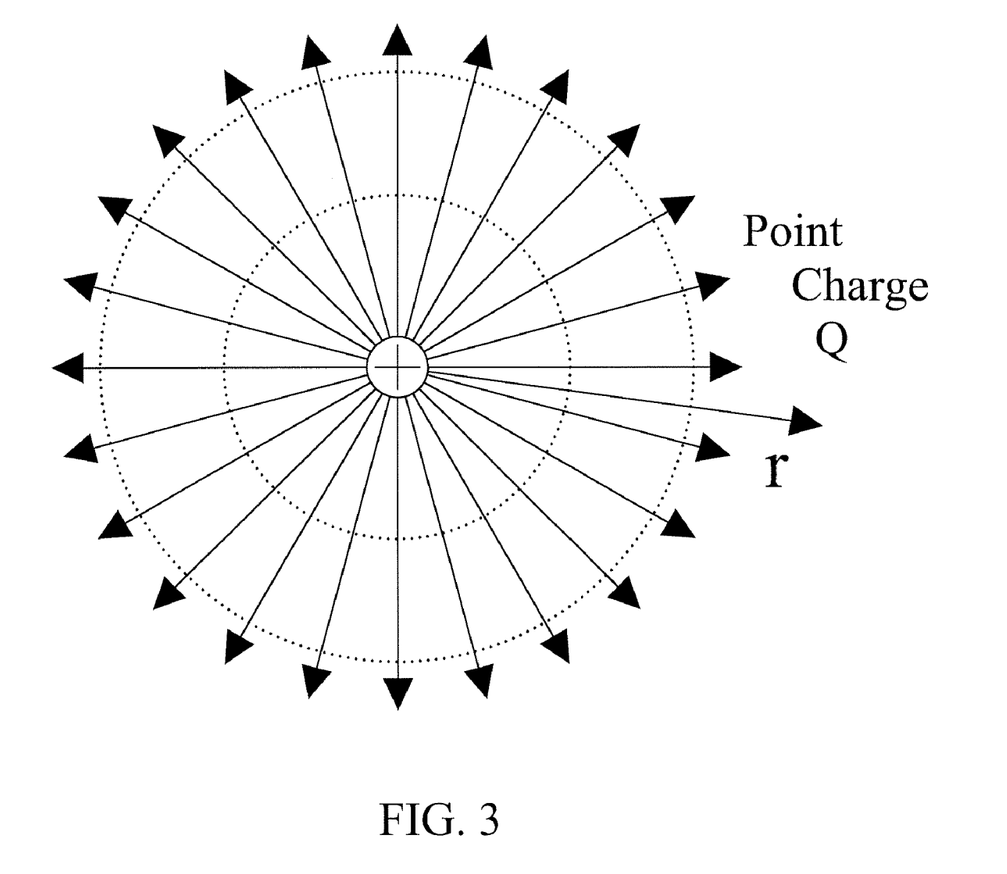

Corona discharge of both the positive and negative variety is commonly characterized as ionization of a neutral atom or molecule in a region of strong electrical field typically in the high potential gradient near a curved electrode, creating a positive ion and a free electron. The electric field then separates and accelerates the charged particles preventing recombination and imparting each particle with kinetic energy. Energized electrons, which have a much higher charge/mass ratio and so are accelerated to a higher velocity, may create additional electron/positive-ion pairs by collision with neutral atoms. These then undergo the same separating process, giving rise to an electron avalanche. Both positive and negative coronas rely on electron avalanches. FIG. 3 illustrates a typical point charge formed in a strong electrical field.

The energy of these plasma processes is converted into initial electron dissociations to seed further avalanches. An ion species created in this series of avalanches, which differs between positive and negative coronas, is attracted to an uncurved electrode, e.g., a flat surface, completing the circuit, and sustaining the current flow.

A corona is a process by which a current, whether or not sustained, develops from an electrode with a high potential gradient in a neutral fluid, usually air. When the potential gradient is large enough at a point in the fluid, the fluid at that point ionizes and it becomes conductive. If a charged object has a sharp point, the air around that point will be at a higher gradient than elsewhere, and can become conductive while other points in the air do not. When the air becomes conductive, it effectively increases the size of the conductor. If the new conductive region is less sharp, the ionization may not extend past this local region. Outside of this region of ionization and conductivity, the charged particles slowly find their way to an oppositely charged object and are neutralized. On the other hand, if the geometry and gradient are such that the ionized region continues to grow instead of stopping at a certain radius, a completely conductive path is formed, and a momentary or continuous spark or arc occurs.

Corona discharge usually involves two asymmetric electrodes, one highly curved, such as the tip of a needle, or a narrow wire, and one of low curvature, such as a plate, or the ground. The high curvature ensures a high potential gradient around one electrode inn order to effectively generate a plasma.

Coronas may be positive or negative. This is determined by the polarity of the voltage on the highly-curved electrode. If the curved electrode is positive with respect to the flat electrode the corona is positive; if the electrode is negative, a negative corona exists. The physics of positive and negative coronas are strikingly different. This asymmetry is a result of the large difference in mass between electrons and positively charged ions, with only the electron having the ability to undergo a significant degree of ionizing inelastic collisions at standard temperatures and pressures.

A negative corona is manifested as a non-uniform corona, varying according to the surface features and irregularities of the curved conductor. It often appears as tufts of corona at sharp edges, the number of tufts changing with the strength of the field. The form of negative coronas is a result of its source of secondary avalanche electrons. It appears a little larger than the corresponding positive corona, as electrons are allowed to drift out of the ionizing region, allowing the plasma to continue some distance beyond it. The total number of electrons and electron density is much greater than in the corresponding positive corona; however, the electrons are at a predominantly lower energy, owing to being in a region of lower potential-gradient. Therefore, while for many reactions the increased electron density will increase the reaction rate, the lower energy of the electrons means that reactions which require a higher electron energy may take place at a lower rate.

A positive corona is manifests as a uniform plasma across the length of a conductor. It is often observed as a blue/white glow, although much of the emission is in the ultraviolet. The uniformity of the plasma is due to the homogeneous source of secondary avalanche electrons. With the same geometry and voltages, a positive corona appears somewhat smaller than the corresponding negative corona, owing to the lack of a non-ionizing plasma region between the inner and outer regions. There are many fewer free electrons in a positive corona, perhaps a thousandth of the electron density, and a hundredth of the total number of electrons, compared to a negative corona, with the exception of the area close to the curved electrode where electrons are highly concentrated. This region has a high potential gradient, causing the electrons to have higher energy. Most of the electrons in a negative corona are in outer, lower energy field areas.

In a positive corona, secondary electrons, giving rise to additional avalanches, are generated predominantly in the fluid itself, in the region outside the plasma or avalanche region. They are created by ionization caused by the photons emitted from that plasma in the various de-excitation processes occurring within the plasma after electron collisions. The thermal energy liberated in those collisions creates photons which are radiated into the gas. The electrons resulting from the ionization of a neutral gas molecule are then electrically attracted back toward the curved electrode and into the plasma, cycling the process of creating further avalanches inside the plasma.

The positive corona is divided into two regions, concentric around the sharp electrode. The inner region contains ionizing electrons, and positive ions, acting as a plasma, the electrons avalanche in this region, creating many further ion/electron pairs. The outer region consists almost entirely of the slowly migrating massive positive ions, moving toward the uncurved electrode along with, close to the interface of this region, secondary electrons, liberated by photons leaving the plasma, being re-accelerated into the plasma. The inner region is known as the plasma region, the outer as the unipolar region.

A negative corona is manifested as a non-uniform corona, varying according to the surface features and irregularities of the curved conductor. It often appears as tufts of corona at sharp edges, the number of tufts altering with the strength of the field. The form of negative coronas is a result of its source of secondary avalanche electrons. The negative corona appears a little larger than the corresponding positive corona, due to drifting of the electrons from the ionizing region, so that the plasma continues some distance beyond it. The total number of electrons, and accordingly the electron density, is much greater than in the corresponding positive corona. The electrons are lower energy that those in a positive corona because they are in a region of lower potential-gradient.

Negative coronas are more complex than positive coronas in construction. As with positive coronas, the establishing of a corona begins with an exogenous ionization event generating a primary electron, followed by an electron avalanche.

The difference between positive and negative coronas is in the generation of secondary electron avalanches. In a positive corona the avalanches are generated by the gas surrounding the plasma region, the new secondary electrons traveling inward, while in a negative corona they are generated by the curved electrode itself, the new secondary electrons traveling outward.

An additional structural feature of negative coronas is the outward drift of the electrons, where they encounter neutral molecules and may combine with electronegative molecules such as oxygen and or water vapor to produce negative ions. These negative ions are then attracted to a positive uncurved electrode, completing the 'circuit'.

A negative corona can be divided into three radial areas, around the sharp electrode. In the inner area, high-energy electrons inelastically collide with neutral atoms and cause avalanches, while outer electrons, usually of a lower energy, combine with neutral atoms to produce negative ions. In the intermediate region, electrons combine to form negative ions, but typically have insufficient energy to cause avalanche ionization. They remain part of a plasma owing to the different polarities of the species present, and the ability to participate in characteristic plasma reactions. In the outer region, only a flow of negative ions and, to a lesser and radially-decreasing extent, free electron movement toward the positive electrode takes place. The inner two regions are known as the corona plasma. The inner region is an ionizing plasma, the middle a non-ionizing plasma. The outer region is known as the unipolar region.

As discussed, the corona principal has been used to create an approximately infinite electric field at the point of a sharp needle. For practical purposes, it can be assumed that the tip of the device is atomically sharp and closely approximates a point charge. This is because as r goes to zero, E approaches infinity. A corona effect is initiated at the tip of the device.

The energy of the electrons and relation to the distance from the point source of generation is based on the electric field of a point charge derived from Coulomb's law. This law states the electric field from any number of point charges can be obtained from a vector sum of the individual fields. A positive number is taken to be an outward field; the field of a negative charge is toward it. This can be shown in equation 1 and illustrated in FIG. 3:

$$E = \frac{F}{q} = \frac{kQ_{source} \, q}{qr^2} = \frac{kQ_{source}}{r^2} \qquad 1$$

EXAMPLES

The following examples are intended only as illustrations of the invention and are in no way to be considered limiting for what is described and taught herein.

Example 1—Apparatus for Molecular Plasma Deposition

An exemplary apparatus includes a vacuum chamber with a small aperture, and a small bore, metallic needle connected to a tube connected to a reservoir holding a liquid suspension or solution of the material desired to be deposited. The reservoir is at atmospheric pressure. A power supply with the ability to supply up to 60 kV can be employed; however, as used in the examples herein, the voltage attached to the needle is typically −5000 volts to +5000 volts. A substrate inside the vacuum chamber, is centered on the aperture with a bias from −60 kV through −60 kV, including ground. The apparatus is illustrated in FIG. 1.

Example 2—Apparatus for Molecular Plasma Generation under Selected Environments The apparatus illustrated in FIG. 2 can be modified such that the needle, tube, and reservoir are disposed in an enclosure that excludes air, but allows for the controlled introduction of other gases. Optionally selected gases include argon, oxygen, nitrogen, xenon, hydrogen, krypton, radon, chlorine, helium, ammonia, fluorine and combinations of these gases.

Example 3—Apparatus for Corona Discharge Generation Under Reduced Pressure

In the apparatus shown in FIG. 1, the pressure differential between the corona discharge and the substrate is about one atmosphere. The outside pressure of the vacuum chamber is approximately 760 Torr, whereas pressure in the area of the substrate is approximately 0.1 Torr.

The apparatus shown in FIG. 2, on the other hand, can be optionally operated at a pre-determined pressure above or below atmospheric pressure. While atmospheric pressure is generally preferred for generation of the plasma, reduced pressure up to about 100 mTorr may in some instances provide satisfactory depositions.

Example 4—Molecular Plasma Deposition of Amino Acids

This example illustrates deposition of a suspension of amino acids onto a gold rod. A colloidal suspension of a mixture of the amino acids glycine (solubility of 20 g/l at 25° C.), alanine (166.5 g/l), valine (88.5 g/l), leucine (24.26 g/l) and arginine (235.8 g/l) in water was deposited using the apparatus of Example 1 onto a gold covered rod, ⅛" in diameter and approximately 0.75 cm². The power supply was attached to a 304 stainless steel 18 gauge needle and set at −5000 V. The gold substrate was set at a potential of 5000 V. The substrate was centered on the hole in the chamber and placed 5 cm from the hole. The vacuum chamber was pumped to 40 mTorr and the flow of the colloidal suspension was initiated. The deposition was carried out for 30 min.

The coated rod was placed in a time-of-flight secondary ion mass spectrometer (TOF-SIMS) and the components were analyzed for composition. Results showed that the amino acids were deposited intact and ionically bonded to the substrate. Mass over charge calculations in conjunction with the time of flight spectrometry were used to calculate the masses of the incoming species. These calculations were used to interpret the spectra from the SIMS. The m/q data showed the amino acids being ejected intact from the surface.

In a control comparison experiment, the substrate was dipped into the amino acid mixture and analyzed by TOF-SIMS as above. These spectra were subtracted from amino acid spectra generated from corona deposition in order to isolate any effects that occurred due only to the deposition method. Fragmentation was observed in both spectra, and after subtraction, it was determined that the fragmentation was an effect of the analytic technique, not the deposition technique because the fragmentation occurred equally in both spectra.

Example 5—Molecular Plasma Deposition of Graphite

A colloidal suspension of graphite powder in isopropyl alcohol (10 g/1001 ml) was deposited onto an aluminum oxide substrate using the apparatus shown in FIG. 1.

The power supply was attached to a 304 stainless steel 18 gauge needle and set at −5000V. The aluminum oxide substrate was connected to ground. The substrate was centered on the hole in the chamber and placed 5 cm from the hole. The vacuum chamber was pumped to 40 mTorr and the flow of the colloidal suspension was initiated. The deposition was carried out for 30 minutes. The substrate was removed from the chamber and a simple ohm meter resistance test performed. Resistance of the substrate changed from infinite to 1 ohm over the 30 min deposition period.

Example 6—Molecular Plasma Deposition of Copper Oxide

A colloidal suspension of copper oxide powder in water (10 g/100 ml) was prepared. Using the apparatus illustrated in FIG. 2, the high voltage power supply was attached to a 304 stainless steel, 18 gauge needle set at −10,000V. The substrate was 304 stainless steel and set at a potential of 5000 V. The substrate was centered and placed 5 cm from the hole in the chamber. The chamber was pumped to 40 mTorr and the flow of the colloidal suspension initiated. The deposition onto the substrate was allowed to proceed for 10 minutes. At the end of the deposition process, the substrate was removed from the chamber and a simple tape test showed good adhesion of the deposited copper oxide. Good adhesion between the substrate and the copper oxide were confirmed by repeating the tape test and by observing that after sonicating the coated sample for 10 min there was no evidence of flaking or sloughing.

Example 7—Molecular Plasma Deposition of RNA and DNA Bases

A colloidal suspension of guanine, adenine, cytosine, uracil and thymine in water (each at 5 g/100 ml) was deposited onto gold covered rod having a surface of approximately 0.75 cm² area, ⅛" diameter, using the apparatus of Example 1. The power supply was attached to a 304 stainless steel 18 gauge needle and set at −5000V. The gold substrate was set at a potential of 5000 V. The substrate was centered on the hole in the chamber and placed 5 cm from the hole. The vacuum chamber was pumped to 40 mTorr and the flow of the colloidal suspension was initiated. The deposition was carried out for 30 min.

The coated rod was placed in a time-of-flight secondary ion mass spectrometer (TOF-SIMS) and the components were analyzed for composition. Results showed that the DNA bases were deposited intact and ionically bonded to the substrate. Mass over charge calculations in conjunction with the time of flight spectrometry were used to calculate the masses of the incoming species.

These calculations were used to interpret the spectra from the SIMS. The m/q data showed the bases being ejected from the surface as being intact. Spectra from another deposition method (dipping the substrate in a mixture containing the bases) ware also analyzed as a control to the bases deposited using the corona effect. The spectra was subtracted from the corona effect spectrum to isolate any effects that occurred due only to the deposition method. Fragmentation was observed in both spectra, and once subtracted, it was determined this observation was a product of the analytic technique and not the deposition technique because the fragmentation occurred equally in both spectra.

Example 8—Molecular Plasma Deposition of Catalase 25 ml of a 2× crystallized bovine liver catalase (Sigma C100-58MG; 056K7010) colloidal suspension in water with 0.1% thymol was prepared. Protein concentration was 33 mg/ml with an activity of $4.1 \times 10^4$ U/ml.

Using the apparatus illustrated in FIG. 2, the high voltage power supply was attached to a 304 stainless steel, 18 gauge needle set at −5000V. The substrate was an aluminum oxide disk ¼" thick by 1.5" in diameter, having an area of approximately 11 sq cm and set at a potential of 5000 V. The substrate was centered and placed 5 cm from the hole in the chamber. The chamber was pumped to 40 mTorr and the flow of the colloidal suspension initiated. The deposition onto the substrate was allowed to proceed for 10 minutes. At the end of the deposition process, the substrate was removed from the chamber and the sample was placed in a 5% solution of hydrogen peroxide. The results showed the catalysis of the hydrogen peroxide by the catalase, producing bubbling of oxygen from the surface, showing that the enzyme remained intact throughout the deposition process.

The deposition was repeated twice under the same conditions, except that after the substrate was removed from the chamber, the samples were placed in an ultrasonic water bath for 10 min. Additionally, one of the samples was maintained at 10° C. for 72 hr after removal from the bath. In each case, exposure of the sample to a 5% solution of hydrogen peroxide produced bubbling of oxygen from the surface of the substrate. The ultrasonic treatment did not affect the deposited material, indicating that a stable, adherent coating of catalase had been deposited.

What is claimed is:

1. A molecular plasma method for deposition of a biomolecule onto a substrate, comprising,
    generating an ionized molecular plasma corona under atmospheric conditions from a biomolecule in a liquid solution or suspension ejected from a conductive point connected to a voltage source sufficient to generate the ionized molecular plasma wherein the biomolecule in solution or suspension becomes charged, yet remains intact; and
    directing the generated plasma through an orifice of an evacuated chamber housing a substrate at an induced potential opposite to the conductive point;
    wherein the biomolecule is deposited onto the substrate without significantly altering the physical, functional or chemical characteristics.

2. The method of claim 1 wherein the suspension is colloidal.

3. The method of claim 1 wherein the liquid is water, alcohol or mixtures thereof.

4. The method of claim 1 wherein the generated corona discharge plasma comprises a positive or negatively charged plasma.

5. The method of claim 1 wherein the biomolecule is an amino acid, a nucleic acid base, or a polypeptide.

6. The method of claim 1 wherein the biomolecule is selected from the group consisting of carbon, copper oxide, an amino acid, an RNA or DNA base, catalase and mixtures thereof.

7. The method of claim 1 wherein the biomolecule is at least one of glycine, alanine, valine, leucine, arginine or mixtures thereof.

8. The method of claim 1 wherein the biomolecule is at least one of guanine, adenine, thymine, cytosine, uracil or mixtures thereof.

9. The method of claim 2 wherein the colloidal suspension is comprised of particles having a size range between about 100 angstroms and about 10,000 angstroms.

10. The method of claim 1 wherein the substrate is a metal, ceramic or a plastic.

11. A molecular plasma method for deposition of a biomolecule onto a substrate, comprising,
    atomizing a solution or liquid suspension of a biomolecule into a partial vacuum from a conductive tip at a voltage sufficient to generate a plasma containing the intact charged biomolecule; and
    directing the plasma through an orifice into an evacuated chamber housing a substrate connected to ground or held at a voltage opposite to the voltage of the conductive tip;
    wherein the biomolecule deposits onto the substrate.

12. The method of claim 11 wherein the biomolecule is selected from the group consisting of carbon, copper oxide, an amino acid, an RNA or DNA base, catalase and mixtures thereof.

13. The method of claim 11 wherein the biomolecule is at least one of glycine, alanine, valine, leucine, arginine or mixtures thereof.

14. The method of claim 11 wherein the biomolecule is at least one of guanine, adenine, thymine, cytosine, uracil or mixtures thereof.

15. The method of claim 11 wherein the liquid suspension is a colloidal suspension comprised of particles having a size range between about 100 angstroms and about 10,000 angstroms.

16. The method of claim 11 wherein the solution or liquid suspension comprises water, alcohol, glycol or combinations thereof.

17. The method of claim 11 wherein the vacuum in the chamber is less than 100 mTorr.

18. The method of claim 11 wherein the voltage applied to the conductive tip is positive or negative in the range of 15,000 volts.

19. The method of claim 11 wherein the liquid is atomized into a vacuum in the range of 100 mTorr up to atmospheric pressure.

20. The method of claim 11 wherein the biomolecule is deposited on the substrate without significantly altering the physical, functional or chemical characteristics.

* * * * *

UNITED STATES PATENT AND TRADEMARK OFFICE
CERTIFICATE OF CORRECTION

PATENT NO. : 7,250,195 B1 Page 1 of 1
APPLICATION NO. : 11/623411
DATED : July 31, 2007
INVENTOR(S) : Daniel M. Storey, Terrence S. McGrath and Tushar M. Shimpi It is certified that error appears in the above-identified patent and that said Letters Patent is hereby corrected as shown below:

<u>Column 5,</u>
Line 62, "Oxidodreductases" should read -- Oxidoreductases --.

<u>Column 12,</u>
Line 16, "alcohol (10 g/1001 ml)" should read -- alcohol (10g/100ml) --.

Signed and Sealed this

Twenty-ninth Day of April, 2008

JON W. DUDAS
*Director of the United States Patent and Trademark Office*